United States Patent [19]

Zangrandi et al.

[11] 4,013,508

[45] Mar. 22, 1977

[54] PROCESS FOR THE PRODUCTION OF 1-ASPARTIC ACID BY FERMENTATION OF HYDROCARBONS

[75] Inventors: Vittorio Zangrandi; Paolo Peri, both of Milan, Italy

[73] Assignee: Liquichimica S.p.A., Milan, Italy

[22] Filed: Nov. 13, 1975

[21] Appl. No.: 631,454

[30] Foreign Application Priority Data

Nov. 21, 1974 Italy .................................. 54163/74

[52] U.S. Cl. .............................. 195/28 R; 195/37; 195/47; 195/111

[51] Int. Cl.² ........................................... C12B 1/00

[58] Field of Search ............ 195/28 R, 30, 111, 96, 195/36, 37, 47, 82

[56] References Cited

UNITED STATES PATENTS 3,214,345  10/1965  Chibata et al. ........................ 195/30
3,793,153   2/1974  Miura ............................... 195/28 R

OTHER PUBLICATIONS

Rose et al., "The Condensed Chemical Dictionary" Van Nostrand Publishing Corp. 1969 p. 433.

Primary Examiner—R. B. Penland
Attorney, Agent, or Firm—Olson, Trexler, Wolters, Bushnell & Fosse, Ltd.

[57] ABSTRACT

Process for the production of 1-aspartic acid by fermentation of hydrocarbons, wherein the fermentation is obtained by contemporaneous or subsequent inoculation of the culture medium with microorganisms of the type *Candida Hydrocarbofumarica* and Bacillus species and that the 1-aspartic acid obtained is the product of the cumulative exocellular metabolism to the account of said hydrocarbons present in said culture medium.

7 Claims, 1 Drawing Figure

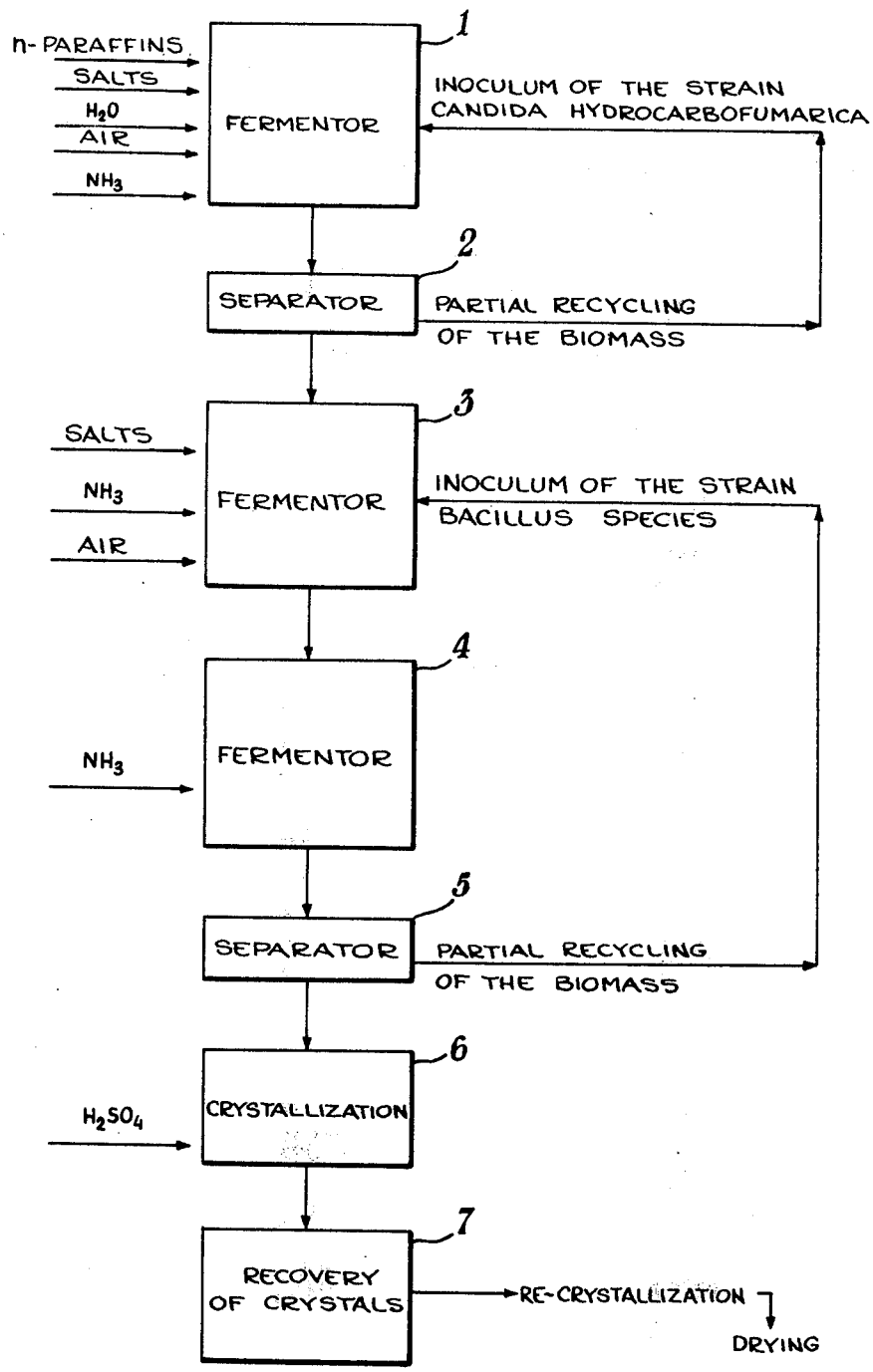

PROCESS FOR THE PRODUCTION OF 1-ASPARTIC ACID BY FERMENTATION OF HYDROCARBONS

The present invention concerns a process for the production of 1-aspartic acid by fermentation of hydrocarbons and, in particular, a process for the production of 1-aspartic acid with the use of, at least, two types of microorganisms. In the process covered by the present invention, two types of microorganisma are used: one is a microorganism strain which assimilates hydrocarbons or fractions thereof, transforming them into fumaric acid and the other is a strain of a different type of microorganism, which does not assimilate hydrocarbons, but transforms the fumaric acid that has been produced into 1-aspartic acid. The 1-aspartic acid obtained by the process covered by the present invention is produced in great amount. The culture medium used may consist, in general, of the following components: hydrocarbons, nitrogen sources, inorganic salts and small amounts of substances stimulating the microbial growth. The process includes also the precipitation and purification of the 1-aspartic acid produced.

The 1-aspartic acid can be utilized in many fields, in relation to its use as: tonic, hepatic regulator, for eliminating the nitrogenous residues, metabolism regulator, myocardium regulator, regulator of neuro-vegetative disorders, food additive, sweetener for beverages, basic intermediate for organic syntheses.

Therefore, the importance of this product and consequently, of the present invention can be easily inferred.

It is known that certain aminoacids accumulate in the culture medium as exocellular products of the metabolism of microorganisms by cultivating certain microorganisms or nutritional substrata containing carbohydrates, especially glucose, starch and molasses hydrolysates, an assimilable source of nitrogen, inorganic salts and some growth factors.

However the present availability of these sources of natural origin is decreasing dramatically, therefore it is justifiable today to turn to other less conventional carbon sources.

It has been also found that some microorganisms are capable of producing aminoacids in culture media containing hydrocarbons or hydrocarbons components as a main source of assimilable carbon. Said microorganisms are not limited in number, as they do not belong to a specific genus, but they have been isolated within the classes of fungi, yeasts, bacteria.

The object of the present invention is to provide a process which permits the obtaining of 1-aspartic acid with a high yield by fermentation of hydrocarbons, with the twofold enormous advantage of applicability of the process on an industrial scale, joined to the availability and low cost of the raw material.

According to what has been previously described, the fermentation covered by the present invention is of the associate type and the microorganisms are of two kinds: the first presents morphologic and physiologic characteristics not dissimilar to those described for the species *Candida Hydrocarbofumarica*, (see Agricultural Biological Chemistry, 34, 670, 1970), the second belongs to the genus Bacillus species.

The main characteristics of the strain of the first organism are: round or slightly oval (3.6 $\mu$), single or in chain formation cells, colonies on agarmalt with smooth or slightly wrinkled surface with an indented edge; not sporiferous; formation of pseudomycelium; presence of blastospores in chain formation or in verticils. It ferments glucose, saccharose, maltose, galactose, lactose; assimilates sorbose, cellobiose, starch, xylose, arabinose, ribose. It does not utilize nitrates, does not liquefy gelatin (ATCC number 20473).

The second microorganism belongs to the genus Bacillus species and presents the following characteristics: single or filamentous bacillary forms (2.8 $\mu$), with oval, motile spores; it liquefies gelatin, grows in nutritional broth with 7% NaCl, it does utilize citrates, hydrolizes starch, produces $H_2SO_4$ during its normal growth and reacts positively to the Voges-Proskauer test. (ATCC number 31177).

In the process covered by the present invention the fermentation occurs at a temperature ranging from 25° to 40° C and the pH of the reaction is neutral.

The hydrocarbons that may be generally used for the production of fumaric acid are specifically n-paraffins containing from 10 to 20 carbon atoms, preferably from 13 to 18. The concentration used is 5–10% w/v.

Since n-paraffins are slightly soluble in water and since a great amount of them has to be added to the broth culture to be metabolized, they have to be well dispersed and micronized in the water and therefore it is necessary a vigorous stirring of the broth culture, a stirring which is facilitated by air bubbling and by the addition of an emulsifying or dispersing additive.

The inorganic sources of nitrogen, used in the present invention, may be ammonium salts, such as ammonium chloride, ammonium sulfate, ammonium phosphate, and ammonium carbonate, ammonia solution or gas, urea, preferably not nitrate.

The sources of organic nitrogen, which are used in small concentration, may be peptone, casein enzymatic hydrolysate, yeast extract, liquid extract of maize, meat flour. The yield of the hydrocarbon metabolizing microorganism is high and reaches 80%, meaning by this number the weight transformation ratio of the supplied paraffins into produced fumaric acid.

The fumaric acid thus obtained constitutes the substratum for the second microorganism in order to obtain, after about three days, the transformation into 1-aspartic acid.

According to the present invention, the culture medium, containing paraffin, mineral salts, sources of assimilable nitrogen, is inoculated with an inoculum mass of the strain which metabolizes paraffin into fumaric acid and the culture is aerobically led under strong stirring to the almost complete transformation of the paraffin into dicarboxylic acid. At this point the direct recovery of fumaric acid or the direct inoculation of the inoculum mass of the strain which catalyzes the transformation into 1-aspartic acid may be performed.

The aeration of the culture medium obtained in the flasks merely by shaking with a vibrator, and in the fermentation containers by stirring and direct aeration, is necessary to ensure a suitable concentration of oxygen dissolved into the culture broth, which is indispensable to the oxydizing metabolism of the n-paraffin and also to obtain a fine dispersion of the n-paraffin itself which is more rapidly attackable by the microorganisms.

During the fermentation the pH of the culture medium is lowered because of a decrease of the substratum basic ratio, with consequent accumulation of acidic anions and the formation of organic acids, wherefore a continuous correction of the culture medium towards neutrality is necessary; this is obtained by the addition of alkali such as ammonia or urea.

Obviously, the fermentation of the two strains may occur at the same time or by an independent sequence.

Referring to the second stage, the metabolism of the fumaric acid has been particularly considered.

During the stage of the Bacillus species growth, only a small portion (about 10%) of the fumaric acid present in the culture broth is transformed into l-aspartic acid. At the end of the stationary stage of growth, the transformation becomes very rapid and a pronounced lysis of the bacterial cells may be observed at the same time.

Evidently, since the aspartase is an endocellular enzyme, as long as the cells are integral, the speed of transformation is limited by the speed of the motion of the reacting substances and the reaction products through the cellular wall.

The stationary stage of growth is contemporaneous with the beginning of the cells lysis and solubilization of the enzyme, wherefore its action is no longer limited by the cellular permeability. During the fermentation it has been observed that not all the fumaric acid which disappears is transformed into l-aspartic acid. By paper chromatography it is possible to detect the presence of malic acid and after titration of this acid, it is possible to ascertain that the malic acid produced corresponds to the difference between the amount of fumaric acid transformed and that of l-aspartic acid produced.

When the concentration of fumaric acid is almost disappeared, that of malic acid also decreases to become almost zero, while the concentration of l-aspartic acid continues to increase until it reaches the maximum value calculated on the basis of fumaric acid which was present in the culture medium. The following hypothesis can be made to explain this phenomenon: besides aspartase which catalyzes the following reaction:

$$\text{fumaric acid} + NH_3 \rightleftarrows \text{aspartic acid} \qquad (1)$$

another enzyme is present, the fumarase which catalyzes the following reaction:

$$\text{fumaric acid} + H_2O \rightleftarrows \text{malic acid} \qquad (2)$$

If it is assumed that in reaction 1 the equilibrium is definitely displaced towards the fermentation of aspartic acid (also on account of the presence of a large excess of ammonia, about twice the stoichiometric amount) and that reaction 2 is also reversible, as long as fumaric acid is present, both reactions will go towards the right, with contemporaneous formation of aspartic acid and malic acid; when fumaric acid has reached a concentration lower than that of equilibrium reaction 2, the direction of this one will be reversed and will continue to go from right to left, since fumaric acid which is formed from malic acid will be utilized in reaction 1 for the formation of l-aspartic acid.

The fermentation is considered to be totally completed when all fumaric acid has been transformed into l-aspartic acid.

In order to effect the recovery of l-aspartic acid, the broth culture which contains ammonium aspartate in the amount of 5–10% w/v, expressed as l-aspartic acid, is acidified with $H_2SO_4$ until it reaches a pH of 4 to 5. The acidified solution is purified by filtration through diatomaceous earth after a previous heating. The filtrate cooled to 10°–18° C, is brought to a pH of 2 to 3 with $H_2SO_4$ under stirring. Under these conditions l-aspartic acid is insoluble, therefore it crystallizes and precipitates. The recovery of the crystals is performed by centrifugation. The degree of purity reaches 90–95% and in order to obtain a higher degree it is necessary to resort to a subsequent crystallization.

The process covered by the present invention is schematically indicated in the attached drawing which refers to the semi-continuous process using two separated and distinct inoculums.

With reference to said drawing, number 1 indicates the fermentation container wherein n-paraffins, salts, $H_2O$, air and $NH_3$, besides the strain of Candida Hydrocarbofumarica, are introduced. From said fermentation container 1 the mass is conveyed into separator 2 where partial separation of the biomass occurs; this is then recycled back into fermentation container 1; in separator 2 the separation of fumaric acid also occurs and this is then conveyed into fermentation container 3. In said fermentation container 3, in the presence of salts, $NH_3$, air and the strain of Bacillus species, the transformation of fumaric acid into l-aspartic acid takes place, and the transformation is completed in subsequent fermentation container 4 in the presence of an excess of $NH_3$. From fermentation container 4 the mass is conveyed into separator 5, where partial separation of the biomass occurs; this is then recycled back to fermentation container 3; then from separator 5 the broth culture is conveyed into crystallizer 6, where, because of the action of $H_2SO_4$ introduced therein, crystallization and separation of crystals of l-aspartic acid occur. Said crystals are then separated in separator 7 and, after a subsequent crystallization and drying, they constitute the final product of the process covered by the present invention.

Some examples of the application of the process covered by the present invention are reported below and these examples are given only as an explanation and not as a limitation of said process.

EXAMPLE 1

A culture broth having the following composition has been prepared:

| | | |
|---|---|---|
| n-paraffins $C_{13} - _{18}$ | 60 | g/l |
| $NH_4Cl$ | 5 | " |
| $K H_2PO_4$ | 1 | " |
| $Mg SO_4 . 7H_2O$ | 0.5 | " |
| $FeSO_4 . 7H_2O$ | 0.03 | " |
| $Mn SO_4 . 4H_2O$ | 0.003 | " |
| $Zn SO_4 . 7H_2O$ | 0.005 | " |
| yeast extract | 0.05 | " |
| peptone (bacto peptone Difco) | 0.05 | " |
| Tween 80 (Polyoxyethylene 20 Sorbitan monooleate) | 0.5 | " |
| water | q.s.* | |

*(quantum sufficit, i.e. a sufficient amount to make the volume identified; in this case, one liter)

After the pH has been adjusted to 7.2, some 500 ml, large neck flasks, containing 50 ml of broth, have been prepared; all of them have been sterilized 15 minutes under ½ atm. (116° C).

A cellular suspension of the strain of the *Candida Hydrocarbofumarica* type has been inoculated into each flask. After 120 hours of incubation at 30° C, under stirring by a reciprocating vibrator, the culture broth has been analyzed and a concentration of 44 g/l of fumaric acid has been found. The broth has been analyzed also for the presence of l-aspartic acid and a concentration of 15 mg/l of said acid has been found.

This concentration, presumably, derives from the autolytic action of the cells of the microorganism itself, as well as from the portion supplied by the source of organic nitrogen and not from a metabolic accumulation to be charged to the n-paraffins.

EXAMPLE 2

A culture medium of the following composition has been prepared:

| Fumaric acid | 60 g/l |
|---|---|
| Ammonia solution 28 % | 6.5 ml |
| $K_2HPO_4$ | 2 g/l |
| $Mg SO_4 . 7H_2O$ | 0.5 g/l |
| yeast extract | 0.5 g/l |
| peptone (bacto peptone Difco) | 0.5 g/l |
| water | q.s. |

After the pH of the solution has been adjusted to 7.2, some 500 ml, large neck flasks, containing 50 ml of broth have been prepared. Said flasks have been sterilized in an autoclave 15 minutes under ½ atm. (116° C).

A cellular suspension of the strain of the Bacillus species type has been inoculated into each flask. After 70 hours of incubation at 30° C, under stirring with a reciprocating vibrator, the culture broth has been analyzed and a concentration of 44 g/l of l-aspartic acid and 17 g/l OF l-malic acid has been found.

EXAMPLE 3

*Candida Hydrocarbofumarica*, a microorganism which assimilates hydrocarbons and produces fumaric acid, has been cultivated on a suitable agar culture medium for a period of 24–48 hours, at a temperature of 30° C. A suspension of cells of the microorganism originated from the agar culture has been inoculated into a 500 ml flask containing 30 ml of a culture medium consisting of:

| $NH_4Cl$ | 0.1–0.5 % by vol. |
|---|---|
| $KH_2PO_4$ | 0.05–0.1 % by vol. |
| $Mg SO_4 7H_2O$ | 0.05–0.1 % by vol. |
| $Fe SO_4 7H_2O$ | 0.003 % |
| $Mn SO_4 4H_2O$ | 0.0003 % |
| Yeast extract | 0.5–0.1 % by vol. |
| n-paraffins | 3–5 % by vol. |
| $H_2O$ | q.s. |

The pH of the culture broth has been adjusted to neutrality with $NH_4OH$ before sterilization. The inoculum culture has been maintained at 30° C for a period of 24–36 hours on a reciprocating vibrator. At this point the biomass was sufficiently grown to inoculate the fermentation stage.

The fermentation stage has been performed in 500 ml flasks with 50 ml of fermentation broth consisting of:

| $NH_4Cl$ | 0.5–4 % by vol. |
|---|---|
| $KH_2PO_4$ | 0.2–0.5 % |
| $Mg SO_4 . 7H_2O$ | 0.05–0.1 % |
| $Fe SO_4 . 7H_2O$ | 0.003 % |
| $Mn SO_4 . 4H_2O$ | 0.003 % |
| $ZnSO_4 . 7H_2O$ | 0.005 % |
| yeast extract | 0.05 % |
| Peptone(bacto peptone Difco) | 0.05 % |
| n-paraffins | 8–10 % |
| $H_2O$ | q.s. |

The pH has been adjusted to neutrality with $NH_4OH$, before sterilization.

Each flask has been inoculated with 2–4 ml of the inoculum culture and incubated at 30° C. with a reciprocating vibrator for 60–70 hours. The culture pH has been adjusted at intervals with $NH_4OH$. After 60–80 hours of incubation, the percentage of n-paraffins transformed was 70–80% and the concentration of fumaric acid present in the broth as ammonium salt was about 60–75 g/l.

The microorganism which transforms fumaric acid into l-aspartic acid has been maintained in agar containing fumaric acid, peptone, potassium phosphate, $(NH_4)_2 SO_4$ as a source of inorganic nitrogen, mineral salts. A 500 ml flask containing 30 ml of the following broth:

| Ammonium fumarate | 3–6 % (by vol.) |
|---|---|
| $K_2HPO_4$ | 0.2–0.4 % (by vol.) |
| $Mg SO_4 7H_2O$ | 0.05–0.1 % (by vol.) |
| Yeast extract | 0.2 % (by vol.) |
| $H_2O$ | q.s. | has been seeded with a culture made on the aforesaid agar.

The pH of the broth has been adjusted to neutrality with $NH_4OH$.

The culture has been maintained in incubation at 30° C for a period of 24 hours on a reciprocating vibrator. After this period the culture contained an amount of cells sufficient to inoculate the 60–70 hours old broth culture of the preceeding fermentation, performed with the use of the strain of the *Candida Hydrocarbofumarica* type.

Subsequently the fermentation is of the mixed type, meaning that the first microorganism brings to completion the transformation of paraffin, the second converts the accumulated fumaric acid into l-aspartic acid. At the same time the second microorganism finds in the previous broth culture some metabolism products which have a stimulation function on the growth. The conversion of fumaric acid into l-aspartic acid occurs in a period of 48–60 hours (for a total period of 120–144 hours), with a conversion yield, referred to n-paraffins, of 60–70%. The concentration of l-aspartic acid in the final broth culture was 45–65 g/l; that of malic acid was 14–18 g/l. The broth has been acidified with $H_2SO_4$ to a pH of 4 to 5. The product has been decolorized with activated carbon in a percentage of 0.2–0.5% at a temperature of 60°–100° C. The precipitate has been filtered through diatomaceous earth and the filtrate has been cooled at 10°–15° C. The cooled filtrate has been again acidified to a pH of 2 to 3 with $H_2SO_4$ under stirring. A precipitation of l-aspartic acid crystals occurred and they have been collected on a filter and dried. The yield of the extraction was about 80% and the purity titer of the crystals obtained was about 90%.

The raw l-aspartic acid has been dissolved by boiling in a container provided with refrigerator, into deionized water, in the ratio 1:20. 1–2% of decolorant charcoal has been added to the solution. The solution has been boiled for a period of 20–30 minutes, and then has been filtered while it was hot and has been let to crystallize under stirring and under cooling at 5° C. The crystals have been recovered by centrifugation. The re-crystallization yield was 80–90%.

EXAMPLE 4

The strain of *Candida Hydrocarbofumarica* type, which metabolizes n-paraffins to fumaric acid, has been cultivated on an agar culture medium containing paraffins at a temperature of 30° C for 24 hours and then inoculated into a 3 liter flask, containing 500 ml of broth having the following composition:

| | | |
|---|---|---|
| n-paraffins | 30 | g/l |
| NH₄Cl | 5 | " |
| KH₂PO₄ | 1 | " |
| Mg SO₄ 7H₂O | 0.5 | " |
| Fe SO₄ 7H₂O | 0.03 | " |
| Mn SO₄ 4H₂O | 0.03 | " |
| Yeast extract | 0.5 | " |
| meat flour | 1 | " |
| Tween 80 (Polyoxyethylene 20 Sorbitan monooleate) | 0.5 | " |
| H₂O | q.s. | |

The broth in the flask has been sterilized 20 minutes in autoclave at 115° C, before inoculation. The development of the inoculum culture occurred at 30° C on a reciprocating vibrator at 100 strokes per minute. The period of incunation necessary to obtain a good cellular growth was 36 hours.

The entire broth culture of the inoculum flask has been transferred into a jar containing 20 l of fermentation broth, having the composition reported hereinafter and maintained in incubation at a constant temperature of 30° C with a stirring speed of 800 rpm and an aeration of 1.5 vol/vol/min.

The pH of the fermenting culture has been adjusted to pH 6.5 by addition of ammonia.

Composition of the fermentation broth:

| Composition of the fermentation broth: | | |
|---|---|---|
| n-paraffins C₁₃ – C₁₈ | 80 | g/l |
| NH₄Cl | 5 | " |
| K H₂PO₄ | 1 | " |
| Mg SO₄ 7H₂O | 0.5 | " |
| Fe SO₄ 7H₂O | 0.03 | " |
| Mn SO₄ 4H₂ | 0.03 | g/l |
| Zn SO₄ 7H₂O | 0.05 | " |
| yeast extract (paste) | 0.5 | " |
| Meat flour | 2 | " |
| Tween 80 (Polyoxyethylene 20 Sorbitan monooleate) | 0.5 | " |
| Water | q.s. | |

The concentration of the fumaric acid after 72 hours of fermentation was 46 g/l. The yeast cells have been separated by centrifugation and the clear broth recovered has been inoculated into the same jar with 500 ml of an inoculum culture previously prepared, of the strain of Bacillus species type which transforms fumaric acid into 1-aspartic acid.

The composition of the broth for the preparation of the second inoculum is the following:

| | | |
|---|---|---|
| Ammonium fumarate | 60 | g/l |
| K₂ HPO₄ | 2 | " |
| Mg SO₂ 7H₂O | 0.5 | " |
| Yeast extract (paste) | 2 | " |

| -continued | |
|---|---|
| H₂O | q.s. |

The broth, after adjustment of the pH to 7 has been distributed into 3 l flasks in the ratio of 500 ml each. The flasks have been sterilized at 115° C in autoclave for 20 minutes. Each flask has been inoculated with a cellular suspension of the strain of Bacillus species type, obtained from a slant of the strain cultivated on agar, containing also fumaric acid, K₂HPO₄, MgSO₄, yeast extract.

The development of the inoculum culture has been performed at 30° C on a reciprocating vibrator at 100 strokes per minute. The period of incubation was of 18 hours. The strain of the Bacillus species inoculated into the broth containing fumaric acid has rapidly grown and has reached the stationary stage of growth in 18–20 hours.

The concentration of 1-aspartic acid in the broth culture, at this point, is only 0.5% w/v. From this moment on, the transformation of the fumaric acid continues rapidly, according to the reaction of enzymatic equilibrium previously indicated and is completed in 56–60 hours.

The final concentration of 1-aspartic acid was 41 g/l. Therefore the conversion yield, in the paraffins — 1-aspartic acid fermentation is 51%.

Ten liters of broth culture have been acidified to pH 4.5 with concentrated H₂SO₄.

20 g of activated carbon have been added to the acidified broth culture and then the mixture has been heated at 85°–90° C for 20 minutes. The product has been filtered through a Buckner filter under vacuum, after addition of 1% w/v of diatomaceous earth and then the filtration cake has been washed with water. The clear filtrate has been concentrated, under vacuum until it has reached a concentration of 1-aspartic acid of 18% w/v.

The clear concentrate, cooled in a water stream, has been acidified under stirring to a pH 3, with H₂SO₄ and the stirring has been continued for 5 hours while the pH has been maintained at 3. Because of the slight water solubility of 1-aspartic acid, the acid crystallizes and precipitates. The precipitation has been completed by bringing the cooling temperature to about 5° C and maintaining the stirring for 10 more hours. The precipitate has been recovered by washing with water at +5° C the collected crystals.

The crystals obtained have been dried under vacuum at 55° C. The weight of the recovered crystals was 342 g (percent recovery 83.75). The purity of the crystals was 92%.

The present invention has been illustrated and described according to preferred embodiments thereof, but it is intended that variations or modifications may be introduced therein, without departing from the scope of the present industrial patent.

Having thus described the present invention, what is claimed is:

1. Process for the production of 1-aspartic acid by fermentation of hydrocarbons, characterized in that the fermentation is obtained by incubation of a hydrocarbon-containing culture medium after inoculation with microorganisms first of *Candida Hydrocarbofumarica* ATCC 20473 and subsequently Bacillus species ATCC 31177 in a cumulative exocellular metabolism whereby to produce 1-aspartic acid.

2. Process for the production of 1-aspartic acid by fermentation of hydrocarbons, according to claim 1, characterized in that the culture medium comprises n-paraffins, containing from 10 to 20 carbon atoms, preferably from 13 to 18 carbon atoms, in a concentration from 5 to 10% w/v, inorganic ammonium salts, organic nitrogen compounds, air and water and that the fermentation temperature is ranging from about 25° to about 40° C and the pH of the reaction is substantially neutral.

3. Process for the production of 1-aspartic acid by fermentation of hydrocarbons according to claim 2, characterized in that the ammonium inorganic salts are selected from ammonium chloride, ammonium sulfate, ammonium phosphate and ammonium carbonate and that the organic nitrogen compounds are selected from ammonia, urea, peptone, casein enzymatic hydrolysates, yeast extract, liquid extract of maize and meat flour.

4. Process for the production of 1-aspartic acid by fermentation of hydrocarbons according to claim 1, characterized in that the microorganism Candida Hydrocarbofumarica metabolizes the hydrocarbons into fumaric acid and the microorganism Bacillus species transforms fumaric acid into 1-aspartic acid.

5. Process for the production of 1-aspartic acid by fermentation of hydrocarbons, according to claim 1 characterized in that the 1-aspartic acid produced is recovered from the culture medium by acidification with $H_2SO_4$, filtration, cooling and subsequent further acidification with $H_2SO_4$ under conditions of agitation.

6. Process for the production of 1-aspartic acid by fermentation of hydrocarbons, according to claim 5 characterized by the fact that with the first acidification the pH is brought at about 4–5, that the filtrate is cooled at 10°–18° C and that the subsequent acidification brings the pH of the filtrate to a value ranging from 2 to 3.

7. Process for the production of 1-aspartic acid by fermentation of hydrocarbons, characterized in that the fermentation is obtained by simultaneous inoculation and cultivation of the hydrocarbon-containing culture medium with microorganisms of Candida Hydrocarbofumarica ATCC 20473 and Bacillus species ATCC 31177 and that the 1-aspartic acid obtained is the product of the cumulative exocellular metabolism.

* * * * *